United States Patent [19]

Tischlinger

[11] 4,051,850
[45] Oct. 4, 1977

[54] DISPOSABLE MEDICAMENT INJECTOR

[76] Inventor: Edward A. Tischlinger, 7 Froghollow Road, East Lyme, Conn. 06333

[21] Appl. No.: 634,034

[22] Filed: Nov. 21, 1975

[51] Int. Cl.² ............................................. A61M 5/00
[52] U.S. Cl. ...................... 128/218 NV; 128/218 DA
[58] Field of Search .................. 128/215, 216, 218 R, 128/218 D, 218 N, 218 NV, 218 C, 218 DA, 214.4, 220, 221, 234, 247

[56] References Cited

U.S. PATENT DOCUMENTS

| | | | |
|---|---|---|---|
| 1,948,982 | 2/1934 | Cutter | 128/218 P |
| 2,894,509 | 7/1959 | Bednarz | 128/218 S X |
| 3,366,286 | 1/1968 | Kloehn | 128/218 C |
| 3,710,794 | 1/1973 | Shields | 128/218 NV |
| 3,851,647 | 12/1974 | Monestere, Jr. et al. | 128/214.4 |
| 3,895,633 | 7/1975 | Bartner et al. | 128/218 DA |

FOREIGN PATENT DOCUMENTS

| | | | |
|---|---|---|---|
| 661,018 | 3/1965 | Belgium | 128/218 R |
| 1,616,204 | 3/1967 | Germany | 128/218 R |

Primary Examiner—John D. Yasko
Attorney, Agent, or Firm—Y. Judd Azulay

[57] ABSTRACT

A disposable medicament injector having a cylindrical barrel closed at one end by a slidable plunger and at the other end by a diaphragm assembly including a flexible wall defining a medicament chamber between the plunger and flexible wall. A needle is positioned in spaced relation to the flexible wall whereby movement of the plunger will cause the medicament to flex the flexible wall toward the needle which will then pierce the wall to establish fluid communication between the medicament chamber and the area at the other end of the needle. A finger grip is retained on the plunger end of the glass barrel by the engagement of the inner and outer surfaces of the barrel by a pair of spaced circumferential walls extending from the finger grip. A nose cap assembly is affixed to the diaphragm end of the glass barrel in a similar manner.

5 Claims, 6 Drawing Figures

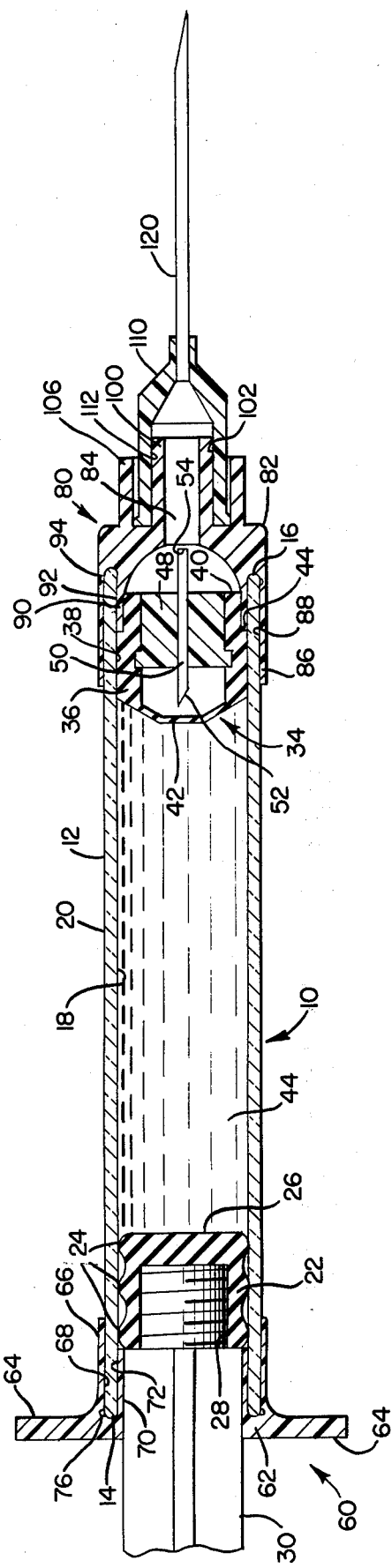
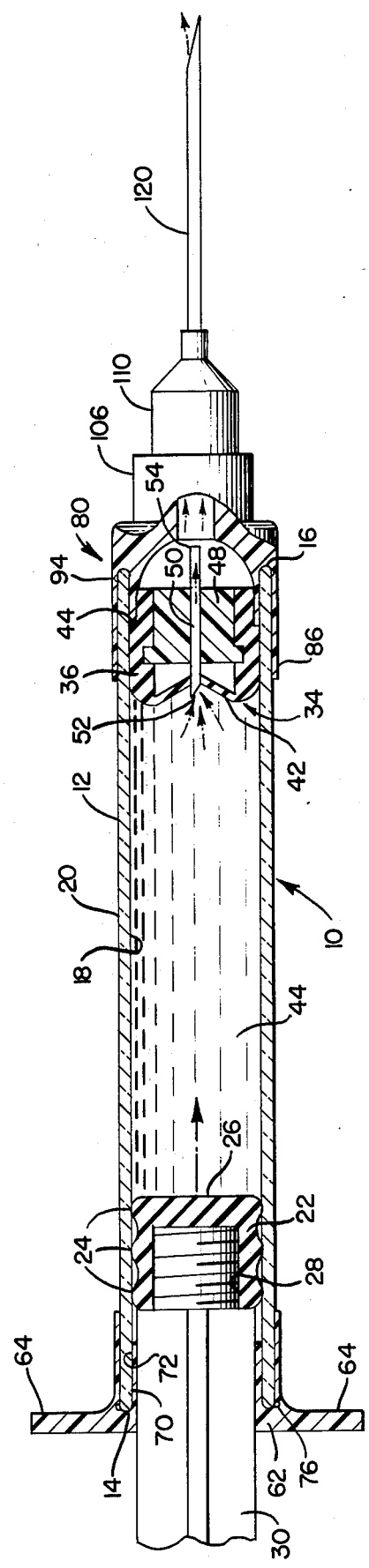
FIG. 1.
FIG. 2.

DISPOSABLE MEDICAMENT INJECTOR

SUMMARY OF THE INVENTION

The field of disposable medicament injectors is quite crowded and yet the needs of the users of such apparatus has not by any means been adequately met. In an effort to provide a disposable medicament injector of great reliability and universal application the injector of this invention has been brought forward.

In view of the foregoing, it is an object of this invention to provide a disposable medicament injector of great reliability and yet extremely simple to use.

It is another object of this invention to provide a disposable medicament injector having a finger grip and a nose cap assembly affixed to the injector's cylindrical barrel solely by interengagement of inner and outer walls of the finger grip and the nose cap assembly with the respective inner and outer surfaces of the cylindrical barrel.

It is yet another object of this invention to provide a disposable medicament injector having a medicament chamber formed by a plunger at one end of the injector barrel and a flexible wall at the other end of the barrel with a needle spaced outwardly from the flexible wall whereby movement of the plunger toward the flexible wall will cause said flexible wall to flex and be pierced by the needle to establish fluid communication between the medicament chamber and the ambient surroundings.

It is a still further object to provide an end member adapted to securely mount on a cylindrical barrel having an inner and an outer surface, the end member comprising a body portion, an outer cylindrical wall extending from said body portion, an inner cylindrical wall extending from the body portion, said inner wall being spaced inwardly from and coaxial with the outer wall, the cylindrical barrel end portion fitting in the space between the two aforesaid walls, the diameters of the inner and outer walls being sized such that the inner surface of the outer wall will snugly engage the outer surface of the barrel and the outer surface of the inner wall will snugly engage the inner surface of the barrel.

The above and additional objects will become more apparent when taken in conjunction with the following detailed description and drawings illustrating a preferred embodiment of this invention.

IN THE DRAWING

FIG. 1 is a longitudinal sectional view of the injector illustrating it in the loaded, ready for use condition;

FIG. 2 is a longitudinal sectional view of the injector illustrating the unit after the plunger has moved forward to flex the diaphragm end wall inwardly for piercing by the needle to allow medicament to flow therethrough;

DETAILED DESCRIPTION OF THE INVENTION

Figure 3:
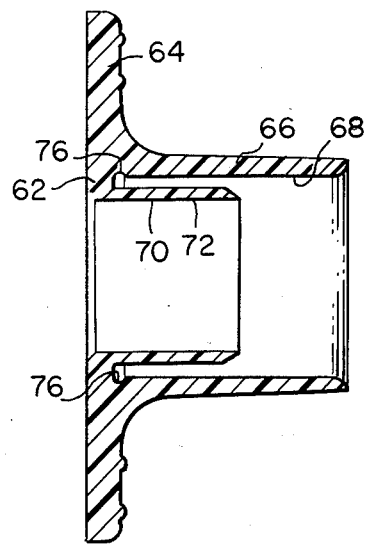
FIG. 3 is a sectional view of the finger grip which is applied to the rear end of the barrel.

As illustrated in FIGS. 1 and 2, the disposable medicament injector 10 comprises a cylindrical glass barrel 12 having an open rear end 14 and an open forward end 16 and an inner surface 18 and an outer surface 20. A rubber plunger 22 is sealingly and slidably carried in the rearward portion of the barrel 12. The plunger 22 is provided with a plurality of circumferential ridges 24 which act as sealing means for the plunger. The forward end of the plunger is closed by an end face 26 while the rear end has a threaded opening 28 adapted to threadedly mount a plunger rod 30.

A diaphragm assembly 34 is positioned in the forward end portion of the barrel 12 and comprises a cylindrical body 36 having an outer surface 38 snugly engaging the inner surface 18 of the barrel 12. The body 36 has an open forward end 40 and a rear end closed by a flexible end wall 42 to form a medicament chamber 44 between said flexible end wall and end face 26 of the plunger 22. The forward portion of the outer surface 38 of the diaphragm body 36 is cut away to a small depth to form a shoulder 44 and circumferential space 46. A needle mount 48 is fitted within the diaphragm body 36 and fixedly carries needle 50 having its rear pointed end 52 spaced from the flexible end wall 42. The forward end 54 of the needle 50 is so positioned that fluid communication is established with the forward end of the barrel 12.

Figure 4:
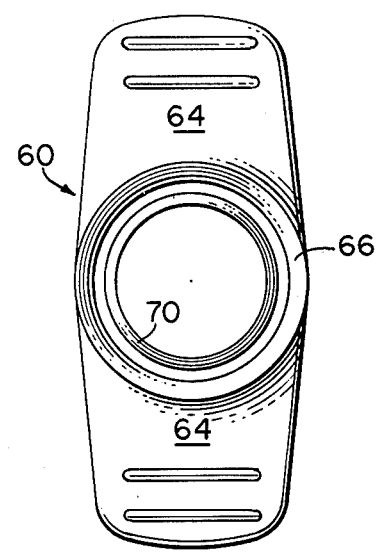
FIG. 4 is an elevational view of the finger grip of FIG. 3 illustrating the finger gripping elements as viewed from the forward end of the finger grip.

Referring to FIGS. 3 and 4 which illustrate the finger grip 60 and to FIG. 1 wherein the finger grip 60 is mounted on the rear end of the barrel 12, said finger grip comprises a circular body portion 62 having a pair of finger grip elements 64, 64 extending diametrically outwardly from said body and generally perpendicular to the longitudinal axis of the glass barrel 12. An outer circumferential wall 66 extends forwardly from the finger grip body 62 and is sized such that the inner surface 68 of the wall 66 snugly engages the outer surface 20 of the glass barrel 12. Similarly, a circular inner wall 70 extends forwardly from the finger grip body 62 and is sized so that its outer surface 72 will snugly engage the inner surface 18 of the glass barrel 12. It is by means of the engagement of the finger grip inner and outer walls 70 and 66, respectively, with the confronting surfaces of the glass barrel 12 that the finger grip is retained thereon. On the inner side where the finger grip body 62 and the outer wall 66 meet there is provided a slight undercut 76 to give a small amount of flexibility to the body 62 and the outer wall 66 during the insertion of the glass barrel 12 into the space between the outer and inner walls, 66 and 70, respectively.

Figure 5:
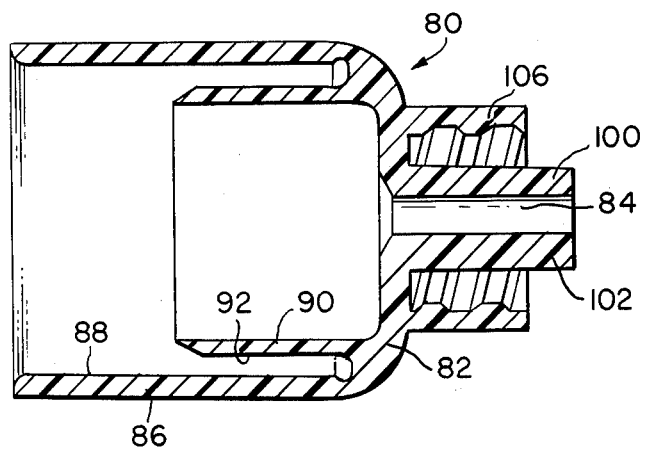
FIG. 5 is a sectional view of the nose cap which is applied to the forward end of the barrel and is adapted to receive various gauges of cannulas.

Referring to FIG. 5 which illustrates one type of nose cap suitable for use and to FIG. 1 wherein the nose cap 80 is mounted on the forward end of the barrel 12, said nose cap includes a circular body portion 82 having a central opening 84 therethrough. An outer circumferential wall 86 extends rearwardly from the circular body portion 82 and is sized so that the inner surface 88 of the wall 86 snugly engages the outer surface 20 of the glass barrel 12. Similarly, a circular inner wall 90 extends rearwardly from the circular body portion 82 and is sized such that the outer surface 92 of the inner wall 90 snugly engages the inner surface 18 of the glass barrel 12. Here again, it is by means of the engagement of the nose cap 80, inner and outer walls 90 and 86, respectively, of the circular body portion 82 with the confronting surfaces on the glass barrel 12 that the nose cap 80 is held thereon. As in the finger grip 60, a slight undercut 94 is formed where the body 82 and outer wall 86 meet to provide a small amount of flexibility for easing the assembly of the nose cap onto the barrel 12. It should be noted that the inner wall 90 is shorter than the outer wall 86 and that its end abuts the shoulder 44 on the diaphragm body 36 to position the diaphragm assembly 34.

A cylindrical bearing 100 projects forwardly from the circular body portion 82 with its longitudinal axis in alignment with the opening 84 in the aforesaid body portion 82. The outer surface 102 of the bearing 100 is provided with a taper corresponding to the standard Luer Lok Taper. Additionally, an internally threaded collar 106 extends outwardly and forwardly from the circular body portion 82 to surround the cylindrical bearing 100. The bearing 100 and collar 106 provide mounting means for various cannula assemblies. More specifically, cannula hub 110 whose inner surface 112 has a taper coinciding with that on the outer surface 102 of the bearing 100 fits on said bearing and supports cannula 120 affixed to the forward end of the hub 110.

In use, the disposable medicament injector 10 as shown in FIG. 1 has a cannula 120 of the desired gauge assembled onto the cylindrical nose cap bearing 100 and the plunger rod 30 is suitably attached to the plunger 22. Forward movement of the plunger 22 under force exerted by plunger rod 30 forces the medicament in chamber 44 forwardly, thus causing the diaphragm assembly end wall 42 to flex forwardly toward the end 52 of needle 50. As shown in FIG. 2, continued flexing in the forward direction causes the needle point 52 to pierce end wall 42 and establish fluid communication between chamber 44 and the cannula 120 for exiting of the medicament. Forward movement of the plunger 22 continues until ejection is complete.

Figure 6:
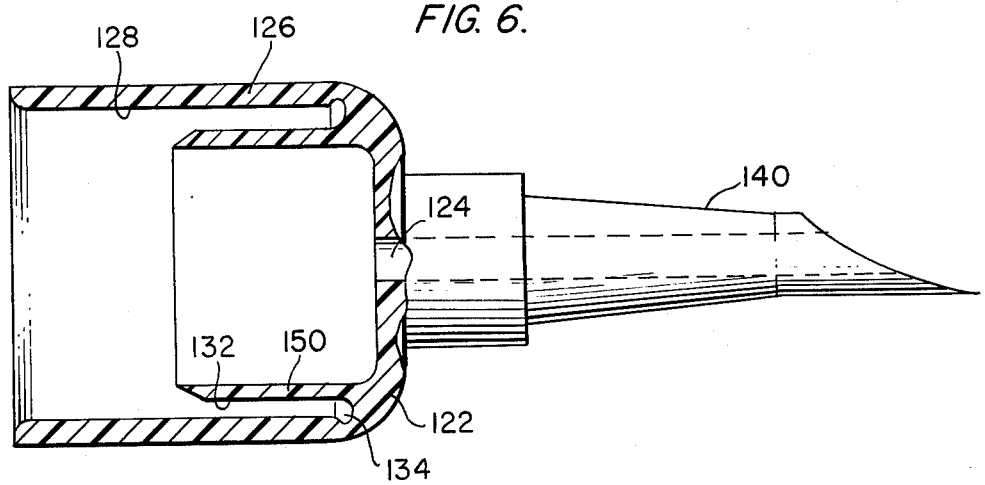
FIG. 6 is a partial sectional view of a combination nose cap and spike adapted to fit on the forward end of the barrel in place of the nose cap of FIG. 5.

The nose cap may be of various types depending upon the intended use. For example, the nose cap could be of the spike type as illustrated in FIG. 6 wherein spike unit 120 comprises a generally circular body portion 122 having a central opening 124 therethrough. An outer circumferential wall 126 extends rearwardly from the body portion 122 and is sized so that the inner surface 128 thereof is adapted to snugly engage the outer surface of a syringe barrel in the manner illustrated in FIGS. 1 and 2. Similarly, a circular inner wall 130 extends rearwardly from the body portion 122 and is sized such that the outer surface 132 thereof is adapted to snugly engage the inner surface of a syringe barrel as in FIGS. 1 and 2. As in the nose cap 60 of FIG. 1, nose cap 120 is provided with an undercut 134 where the body portion 22 and the outer wall 126 meet and is for the same purpose as in the embodiment of FIG. 1. A spike member 140 extends forwardly from the body portion 122 to complete the spike type nose cap.

Additional nose cap assemblies may be used in this syringe combination, the only limitation with regard to structure being that such nose cap must have the two coaxially extending walls adapted to fit over and grip the inner and outer walls of the syringe barrel so as to retain the nose cap thereon.

There are numerous advantages derived from the injector unit of this invention. First of all, almost limitless cannula gauges may be employed. Secondly, virtually any medicament can be stored in the device. As in now apparent, the normal way to ship and store the injector unit would be without the cannula assembly and, of course, the plunger rod would not be assembled to the plunger. Savings in space for storage purposes is immediately apparent. Thirdly, the unit is the ultimate in simplicity and reliability. Further, this injector is quite economical to manufacture. This economy is brought about by many factors including the manner in which the finger grip and nose cap are assembled onto the glass barrel.

Further, in connection with the mounting of the finger grip 60 and the nose cap 80 onto the glass barrel 12, it should be noted that in this particular instance both the finger grip and nose cap are made of polypropylene which is a plastic having the desirable characteristic of retaining its memory after molding, i.e.: retains its size to a very close tolerance. Obviously, any other plastic having these same characteristics would also be suitable.

Plastic, including polypropylene as used herein, like most other materials will expand and contract due to temperature changes and possible humidity changes. Thus, with both the inner and outer walls of the finger grip snugly engaging the respective surfaces of the glass barrel, the finger grip will always be held onto said barrel. More particularly, if the finger grip outer wall expands and becomes slightly loose, the finger grip inner wall will also expand and provide tighter than normal engagement to overcome this. The reverse will be true if cooling takes place, i.e.: the outer wall contracts to firmly grip the glass barrel as the inner wall somewhat loosens its engagement with the barrel.

In view of the above, it should now be apparent that no additional means are needed to retain the finger grip and the nose cap firmly assembled on the glass barrel. This eliminates use of adhesives or cooperating distortedly shaped elements on mating surfaces of the respective parts.

What is claimed is:
1. A disposable medicament unit comprising:
a cylindrical barrel having inner and outer surfaces and open on both its front and rear ends,
a plunger slidably carried in the rear end of the barrel in sealingly relation to the inner surface of the barrel,
a diaphragm assembly fixedly mounted in the forward end of the barrel, said diaphragm assembly including a hollow body portion having inner and outer surfaces, said hollow body portion fitting within the cylindrical barrel with its outer surface sealingly engaging the inner surface of said cylindrical barrel, a flexible wall closing off one side of the body portion to form a medicament chamber between the plunger and the flexible wall, a needle supported by the hollow body portion, said needle being spaced from the flexible wall and outside the medicament chamber, said needle being adapted to pierce the flexible wall when said wall is flexed into contact therewith to establish fluid communication between the medicament chamber and the needle,
a nose cap assembly fitting on the forward end of the barrel, and
a finger grip assembly on a rear end portion of the cylindrical barrel, and the finger grip assembly comprises a body portion with finger gripping elements extending outwardly therefrom and an inner and an outer wall extending forwardly from said body and spaced from each other so as to snugly receive the rear end portion of the barrel therebetween.

2. The invention as set forth in claim 1 and wherein the finger grip is made from a plastic having excellent memory characteristics so that it will retain its shape and thus be subject to dimensional change only by temperature variations.

3. A disposable medicament unit comprising:
a cylindrical barrel having inner and outer surfaces and open on both its front and rear ends,
a plunger slidably carried in the rear end of the barrel in sealingly relation to the inner surface of the barrel,
a diaphragm assembly fixedly mounted in the forward end of the barrel, said diaphragm assembly including a hollow body portion having inner and outer surfaces, said hollow body portion fitting within the cylindrical barrel with its outer surface sealingly engaging the inner surface of said cylindrical barrel, a flexible wall closing off one side of the body portion to form a medicament chamber between the plunger and the flexible wall, a needle supported by the hollow body portion, said needle being spaced from the flexible wall and outside the medicament chamber, said needle being adapted to pierce the flexible wall when said wall is flexed into contact therewith to establish fluid communication between the medicament chamber and the needle,
a nose cap assembly fitting on the forward end of the barrel, and
this nose cap assembly includes a body portion with an inner and an outer wall extending rearwardly therefrom and being spaced so as to snugly receive the forward end portion of the barrel therebetween.

4. The invention as set forth in claim 3 and wherein the nose cap is provided with means adapted to receive a cannula on its forward portion.

5. A disposable medicament injector comprising:
a cylindrical glass barrel open at both its rear and forward ends and having an inner and an outer surface,
a plunger slidably carried in the barrel adjacent the rear end thereof, said plunger sealingly engaging the inner surface of the barrel,
a diaphragm assembly mounted in the forward end of the barrel, said diaphragm assembly comprising a cylindrical diaphragm body snugly engaging the inner surface of the barrel, the forward end of the diaphragm body being open and the rear end being closed by a flexible end wall to form a medicament chamber between the plunger and the aforesaid flexible end wall, a needle mount fitted within the diaphragm body, a needle carried by said needle mount, the rear end of the needle being spaced from the flexible end wall whereby when the plunger is forced forwardly the end wall will flex and be brought into contact with the rear end of the needle to cause the needle to pierce the end wall and allow the medicament to flow through the needle,
a finger grip mounted on the rear end of the barrel, said finger grip including a circular body with a pair of finger grip elements extending diametrically outward from the body and generally perpendicular to the glass barrel, an outer and an inner wall extending forwardly from the circular body and spaced from each other a distance equivalent to the thickness of the glass barrel to form a barrel receiving space whereby the glass barrel is inserted into the aforesaid space so that the inner and outer surfaces of the barrel are snugly gripped by the respective and confronting surfaces on the inner and outer walls,
a nose cap mounted on the forward end of the barrel, said nose cap including a body portion having a central opening therethrough, inner and outer walls extending rearwardly from the body portion, said inner and outer walls being spaced from each other to form a space into which the forward end of the barrel is inserted whereby the inner and outer faces of the barrel are gripped by the confronting surfaces of the inner and outer walls to retain the nose cap in the barrel, and
cannula hub receiving means extending forwardly from the nose cap body and in fluid communication with the opening in said body, said cannula hub receiving means being adapted to mount a cannula assembly which is in fluid communication with the cannula hub receiving means.

* * * * *